United States Patent [19]

Julia

[11] 4,028,422

[45] June 7, 1977

[54] OLEFINIC SULFONES

[75] Inventor: Marc Julia, Paris, France

[73] Assignee: Agence Nationale de Valorisation de la Recherche (ANVAR), Neuilly sur Seine, France

[22] Filed: June 23, 1975

[21] Appl. No.: 589,555

[30] Foreign Application Priority Data

June 25, 1974 France .............................. 74.22004

[52] U.S. Cl. .................. 260/607 AR; 260/607 AL; 260/677 R
[51] Int. Cl.² ....................... C07C 147/08
[58] Field of Search ............... 260/607 AL, 607 AR

[56] References Cited

UNITED STATES PATENTS

| | | | |
|---|---|---|---|
| 3,781,313 | 12/1973 | Julia ............................ | 260/607 AR |
| 3,848,000 | 11/1974 | Chabardes et al. ......... | 260/607 AL |
| 3,850,991 | 11/1974 | Chabardes et al. ......... | 260/607 AL |
| 3,865,878 | 2/1975 | Chabardes et al. ......... | 260/607 AL |
| 3,876,707 | 4/1975 | Menet et al. ................. | 260/607 AL |

*Primary Examiner*—Delbert R. Phillips
*Attorney, Agent, or Firm*—Christie, Parker & Hale

[57] ABSTRACT

Olefinic sulfones of the general formula:

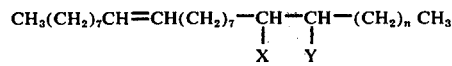

wherein one of X and Y represents a hydrogen atom and the other represents an -SO$_2$-Ar radical in which Ar represents an aryl radical and $n$ is an integer from 1 to 3, the >CH-SO$_2$Ar group may be reduced to a methylene group to give Olefins which are known sexual attractants for flies.

9 Claims, No Drawings

OLEFINIC SULFONES

The present invention relates to new olefinic sulfones, their preparation and their use in the synthesis of biologically active products.

More precisely, the present invention relates to sulfones of the general formula;

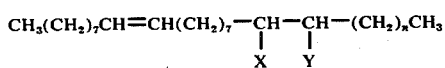 (I)

in which one of the symbols X and Y represents a hydrogen atom and the other represents a $-SO_2-Ar$ radical in which Ar represents an aryl radical possibly substituted by one or more halogen atoms or alkyl radicals containing 1 to 5 carbon atoms (such as phenyl, naphtyl, halogenophenyl, tolyl, xylyl) and $n$ represents an integer from 1 to 3, preferably 1 or 3, as well as their preparation.

Owing to the presence of an ethylenic bond in their molecule, the products of general formula (I) exist in cis and transforms and it is understood that the present invention relates to products in either form as well as to their mixtures.

According to the present invention, the products of general formula (I) may be prepared by the action of a product of general formula:

 (II)

on a product of general formula:

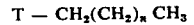 (III)

in which one of the symbols Q and T represents a $-SO_2-Ar$ radical in which Ar is defined as previously and the other symbol represents an active ester residue such as a halogen atom, in particular a bromine atom, a sulphuric ester residue, such as the methyloxysulfonyloxyl radical, or a sulfonic ester residue, such as the p.toluenesulfonyloxyl radical and $n$ is defined as previously.

Generally, this reaction is carried out by mixing products of the general formulae (II) and (III), used in a molar ratio 1:1 in the presence of a basic agent having sufficient activity to anionize the sulfone used. The alkaline agent used may be chosen from oxides or hydroxides of alkaline metals, hydrides, amides or alcoholates of alkaline metals. It is thus possible to use an active metallation agent such as an organomagnesium, organolithium or organozinc. The quantity of alkaline agent may vary from 1 to 1.2 moles per mole of sulfone. In general, a molar ratio of 1:1 is suitable.

The reaction may be carried out at a temperature of approximately 20° C or at lower temperatures which may reach $-80°$ C and preferably in a solvent which is inert under the reaction conditions, such as an aliphatic or aromatic hydrocarbon, an alcohol, an aliphatic or cyclic ether, such as tetrahydrofuran, a polar solvent.

The products of general formula (II) in which Q represents a $-SO_2-Ar$ radical defined as previously may be prepared from a product of general formula (II) in which Q represents a halogen atom, by the action of an arylsulfinate of general formula:

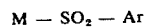 (IV)

in which Ar is defined as previously and M represents an alkaline metal atom, in particular atom of sodium or potassium.

The products of general formula (III) in which T represents a $-SO_2-Ar$ radical defined as previously may be prepared by the action of a sulfinate of general formula (IV) on a product of general formula (III) in which T represents a halogen atom.

These reactions are generally carried out in an organic solvent such as dimethylformamide at a temperature of approximately 20° C or a saturated aliphatic alcohol such as methanol or ethanol refluxed from the reaction mixture.

The products of general formule (I) are useful intermediaries for the preparation of products of the general formula:

 (V)

in which $n$ is defined as previously.

Products of this type, in particular cis — tricos — 9 — ene and cis — heneicos — 9 — ene which were initially isolated from the epidermis or excrement of the female domestic fly are known to be sexually attractive to the male domestic fly [D. A. CARLSON and coll., Science, 174, 76 (1971), A. MANSINGH and coll., Can. Entomol., 1972, 104 (12), 1963-5]. These products use in combination with sterilization processes of male domestic flies (such as irradiation) are useful for fighting against these insects.

Hitherto products of this type were prepared chemically by application of the WITTIG method. Thus, cis — and trans — tricos — 9 — ene were prepared from 1 — bromo tetradecane, triphenylphosphine and nonanal.

The present invention also relates to a method for the preparation of products of general formula (V) in which $n$ is defined as previously, by the action of a reduction agent on a sulfone of general formula (I). As the reduction agent, it is possible to use any agent capable of transforming a $CH-SO_2-Ar$ group, in which Ar is defined as previously, into a methylene group, whilst preserving the ethylenic bond present in the molecule. Alkaline metals may be used in particular as the reduction agent, such as sodium and potassium, in the form of their amalgams or amides derived from saturated aliphatic primary amines containing 1 to 5 carbon atoms, or electrolysis. When an amalgam of an alkaline metal is used, the quantity of amalgam used is such that the molar quantity of alkaline metal is at least double that of the sulfone of general formula (I). The operation is generally carried out at a temperature of approximately 20° C or at lower temperatures which may reach $-50°$ C and in an organic solvent such as an alcohol (such as methanol) or a non-hydroxyl solvent (such as an aliphatic or aromatic hydrocarbon, an aliphatic or cyclic ether) mixed with an alcohol or with water.

When an alkaline metal amalgam is used as the reduction agent, an arylsulfinate of general formula (IV) is formed during the reaction, which may be recovered in order to be used for the preparation of the products of general formulae (II) and (III) as above-mentioned.

The following non-limiting examples show how the invention may be used.

EXAMPLE 1

1.96g ($5.10^{-3}$ mole) oleylphenylsulfone in solution in 10cm³ tetrahydrofuran are treated by the equivalent of butyl lithium at −78° C. The temperature is then allowed to rise progressively to 20° C. During this rise in temperature, the lithiated sulfone crystallises in the medium in the form of white crystals. The reaction mixture is once more cooled to −30° C and 0.76g ($5.10^{-3}$ mole n. pentyl bromide in solution in 5cm³ tetrahydrofuran are added thereto. After having kept the mixture at −30° C for 10 minutes, the temperature is allowed to rise to 20° C and stirring is continued for 2 hours. The reaction mixture is then hydrolyzed by a saturated aqueous solution of ammonium chloride and extracted three times with 50cm³ ether. The combined ethereal extracts are washed three times with a saturated aqueous solution of sodium chloride, dried over magnesium sulphate and concentrated. 2.14g (yield: 93%) of 6-phenylsulfonyl-cis-tricos-14-ene identified by thin layer chromatography and spectrography are thus obtained.

| NMR Spectra: | |
|---|---|
| $C_6H_5 - SO_2 - CH -$ | 4 – 3.5 ppm (m, 1 H) |
| $CH_3$ terminal | 0.87 ppm (m, 6 H) |
| $CH_2$ allyl | 2 ppm (m, 4H) |
| $CH = CH$ | 5.40 ppm (m, 2 H) |
| I.R. Spectra | |
| $C_6H_5$ | 3030 – 1580 cm$^{-1}$ |
| $SO_2$ | 1300 – 1150 cm$^{-1}$ |
| $CH = CH$ cis | 725 cm$^{-1}$ |
| Mass | |
| m/e = 462 | |

The initial oleylphenylsulfone may be prepared in the following manner: a mixture of 16.5g ($5.10^{-2}$ mole) oleyl bromide and 8.2g ($5.10^{-2}$ mole) sodium phenyl sulphinate in 100cm³ dimethylformamide is stirred for 15 hours at 25° C. The reaction mixture is then poured into 800cm³ iced water and the organic phase is extracted five times with ether. The combined ethereal extracts are washed with a saturated aqueous solution of sodium chloride then dried over magnesium sulphate and concentrated. The residue obtained is purified by being passed over a silica column (elution solvent: cyclohexane). By concentration of the eluate, 15g (yield: 77%) oleylphenylsulfone are obtained in the form of a colourless oil identified by NMR and infrared spectrography.

| NMR Spectra: | |
|---|---|
| $CH = CH$ | 5.40 ppm (m, 2 H) |
| $CH_2$ allyl | 2 ppm (m, 4 H) |
| $(CH_2)_{12}$ | 1.30 ppm (m, 2 H) |
| $CH_3$ terminal | 0.87 ppm (m, 3 H) |
| $C_6H_5SO_2$ | 8 – 7.5 ppm (m, 5 H) |
| $CH_2 - SO_2$ | 3.10 ppm (t, 6, 5H$_2$, 2H) |
| I.R. Spectra | |
| $C_6H_5$ | 3030 – 1580 cm$^{-1}$ |
| $SO_2$ | 1300 – 1150 cm$^{-1}$ |
| $HC = CH$ cis | 725 cm$^{-1}$ |
| Mass | |
| m/e = 392 | |

EXAMPLE 2

Proceeding as described in example 1, but with 2.12g ($10^{-2}$ mole) n.pentylphenylsulfone in 20 cm³ tetrahydrofuran, 1 equivalent of butyl lithium and 3.31g ($10^{-2}$ mole) oleyl bromide, 4.62g (yield = 100%) 5-phenylsulfonyl-cis-tricos-14-ene are obtained, identified by thin layer chromatography and spectrography ($n_D^{20}$ = 1.4943).

EXAMPLE 3

1 equivalent of butyl lithium is added slowly to 3.7g ($2.10^{-2}$ mole) n.propylphenylsulfone in 100 cm³ tetrahydrofuran at −78° C. The reaction mixture is stirred for 1 hour allowing the temperature to rise to 20° C, then is once more cooled to −30° C. A solution of 8.44g ($2.10^{-2}$ mole) of oleyl tosylate in 10 cm³ of tetrahydrofuran are added slowly to the yellow solution obtained. The reaction mixture, which turns red in colour, is stirred for 4 hours at 20° C, then hydrolyzed by a saturated iced aqueous solution of ammonium chloride. The organic phase is extracted with ether. The ethereal extracts are washed in water then dried over magnesium sulphate and concentrated. 8.9g of a yellow oil are thus obtained, which oil is identified by thin layer chromatography and NMR spectrography as being 3-phenylsulfonyl-cis-heneicos-12-ene mixed with approximately 25% of the initial oleyl tosylate.

| N.M.R. Spectra | |
|---|---|
| $CH = CH$ | 5.4 ppm (m) |
| $CH - SO_2$ | 3.6 ppm (m) |
| $CH_2$ allyl | 2.0 ppm (m) |
| $(CH_2)_{14}$ | 1.3 ppm (m) |
| $CH_3$ | 0.9 ppm (m) |
| $C_6H_5$ | 7.4 – 8.0 ppm (m) |
| Refraction index | |
| $n_D^{20}$ = 1.4989 | |

The initial oleyl tosylate may be prepared in the following manner: 24g (0.125 mole) tosyl chloride are added slowly to a solution, cooled to 0° C, of 26.8g (0.1 mole) of oleic alcohol in 25 cm³ pyridine. The reaction mixture is then stirred for 15 hours at 20° C, then neutralised by the addition of dilute aqueous hydrochloric acid. The organic phase is extracted with 5 liters in all of a mixture of pentane-methylene chloride (4:1 in volumes). The extracts are washed with an aqueous solution of sodium bicarbonate then with water, dried over magnesium sulphate and concentrated. 38.0g (yield: 90%) of a viscous colourless oil are thus obtained, which oil is identified by thin layer chromatography and NMR spectrography as being oleyl tosylate.

| NMR Spectra | |
|---|---|
| $CH = CH$ | 5.4 ppm (m, 2 H) |
| $CH_2 - O$ | 3.9 ppm (t complex, 2 H) |
| $CH_2$ allyl | 2.0 ppm (m, 4 H) |
| $(CH_2)_{12}$ | 1.3 ppm (m, 4 H) |
| $CH_3$ | 0.9 ppm (m, 3 H) |
| $- C_6H_4 - CH_3$ | 2.4 ppm (s, 3 H) |
| H aromatic | 7.2 – 7.8 ppm (m, 4 H) |
| I.R. Spectra | |
| $CH = CH$ cis | 725 cm$^{-1}$ |
| $- O - SO_2$ | 1170, 1350 cm$^{-1}$ |
| $C_6H_5$ | 1580 cm$^{-1}$ |

EXAMPLE 4

Proceeding as in example 3, but with 4.24g ($2.10^{-2}$ mole) n.pentylphenylsulfone in solution in 100 cm³ tetrahydrofuran, 1 equivalent of butyl lithium and 8.44g ($2.10^{-2}$ mole) oleyl tosylate, 9.8g of a yellow oil are obtained, which is identified by thin layer chromatography and NMR spectrography as being constituted as regards its major part by 5-phenylsulfonyl-cis-tricos-14-ene.

EXAMPLE 5

2.31g ($5.10^{-3}$ mole) 6-phenylsulfonyl-cis-tricos-14-ene (prepared as described in example 1) or 5-phenylsulfonyl-cis-tricos-14-ene (prepared as described in example 2) in 20 cm³ ethanol are stirred for 15 hours at a temperature of 20° C with 8g (4 equivalents of sodium) 6% sodium amalgam. The reaction mixture is poured into 100 cm³ cold water. After triple extraction by 50 cm³ pentane and concentration of the extracts, a residue is obtained which is purified by being passed over a silica column (elution solvent: pentane). After concentration of the eluates, 1.50g (yield: 53%) of a colourless oil are obtained, which oil is identified by gas phase chromatography and spectrography as being cis-tricos9-ene by reference to an authentic sample.

| NMR spectra | |
|---|---|
| CH = CH | 5.30 ppm (t, 5 Hz, 2 H) |
| CH₂ allyl | 2 ppm (m, 4 H) |
| (CH₂)₁₇ | 1.5 – 1 ppm (m, 34 H) |
| CH₃ terminal | 0.88 ppm (m, 6 H) |
| L.R. Spectra | |
| = C — H | 3020 cm⁻¹ |
| CH = CH cis | 725 cm⁻¹ |
| Mass | |
| m/e = 322 | |
| Refraction Index | |
| $n_D^{20}$ = 1.4529 | |

EXAMPLE 6

16g (4 equivalents of sodium) of sodium amalgam are added to 4.5g crude 3-phenylsulfonyl-cis-heneicos-12-ene prepared as described in example 3, in 50 cm³ methanol and the reaction mixture is stirred for 15 hours at 20° C. The reaction mixture is poured into 200 cm³ iced water. After extraction with pentane, washing of the extracts with an aqueous solution of ammonium chloride, then with water, drying over magnesium sulphate and concentration, a residue is obtained which is purified by being passed over an alumina column (elution solvent: pentane). By concentration of the eluate, 1.40 g of a colourless oil are obtained, constituted by cis-heneicos-9-ene (purity determined by vapour phase chromatography: 80%).

| NMR Spectra | |
|---|---|
| CH = CH | 5.4 ppm (m, 2 H) |
| CH₂ allyl | 2.0 ppm (m, 4 H) |
| (CH₂)₁₄ | 1.3 ppm (m, 28 H) |
| CH₃ | 0.9 ppm (m, 6 H) |
| I.R. Spectra | |
| = C — H | 3020 cm⁻¹ |
| Refraction index | |
| $n_D^{20}$ = 1.4517 | |

EXAMPLE 7

Proceeding as described in example 6, but with 5g crude 5-phenylsulfonyl-cis-tricos-14-ene, prepared as described in example 4 and 16g 6% sodium amalgam, 1.67g of a colourless oil are obtained, which oil is constituted by cis-heneicos-9-ene (purity determined by vapour phase chromatography: 75%).

What is claimed is:

1. Olefinic sulfones of the general formula:

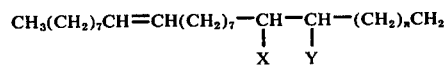

wherein one of X and Y is a hydrogen and the other a —SO₂—Ph radical wherein Ph is selected from the group consisting of an unsubstituted phenyl radical and a substituted phenyl radical having at least one substituted group selected from a halogen atom and an alkyl radical containing from 1 to 5 carbon atoms and wherein $n$ is an integer from 1 to 3.

2. Sulfones according to claim 1 wherein $n$ is 1 or 3.

3. Olefinic sulfones according to claim 1, in the cis configuration.

4. Olefinic sulfones of the general formula:

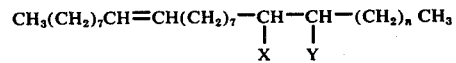

wherein one of X and Y is a hydrogen atom and the other the phenylsulfonyl radical and wherein $n$ is 1 or 3.

5. Olefinic sulfones according to claim 4, in the cis configuration.

6. 6-phenylsulfonyl-cis-tricos-14-ene.
7. 6-phenylsulfonyl-cis-tricos-14-ene.
8. 3-phenylsulfonyl-cis-beneicos-12-ene.
9. 4-phenylsulfonyl-cis-beneicos-12-ene.

* * * * *

UNITED STATES PATENT AND TRADEMARK OFFICE
CERTIFICATE OF CORRECTION

PATENT NO. : 4,028,422
DATED : June 7, 1977
INVENTOR(S) : Marc Julia

It is certified that error appears in the above-identified patent and that said Letters Patent are hereby corrected as shown below:

Column 5, line 19, "cis-tricos9-ene" should read --cis-tricos-9-ene--.

Column 6, line 21, $$\text{"}CH_3(CH_2)_7CH = CH(CH_2)_7 - \underset{X}{\overset{}{CH}} - \underset{Y}{\overset{}{CH}} - (CH_2)_n CH_2\text{"}$$

should read $$--CH_3(CH_2)_7CH = CH(CH_2)_7 - \underset{X}{\overset{}{CH}} - \underset{Y}{\overset{}{CH}} - (CH_2)_n CH_3--.$$

Signed and Sealed this

Twentieth Day of September 1977

[SEAL]

*Attest:*

RUTH C. MASON
*Attesting Officer*

LUTRELLE F. PARKER
*Acting Commissioner of Patents and Trademarks*